United States Patent
Kitazono et al.

(10) Patent No.: US 6,797,280 B1
(45) Date of Patent: Sep. 28, 2004

(54) PRESSURE-SENSITIVE ADHESIVE COMPOSITION AND MOISTURE-PERMEABLE PRESSURE-SENSITIVE ADHESIVE TAPE, PRESSURE-SENSITIVE ADHESIVE DRUG COMPOSITION, AND PRESSURE-SENSITIVE ADHESIVE TAPE PREPARATION EACH CONTAINING THE COMPOSITION

(75) Inventors: Eiichi Kitazono, Iwakuni (JP);
Hiroyoshi Minematsu, Iwakuni (JP);
Takeyuki Kawaguchi, Iwakuni (JP);
Takanori Miyoshi, Iwakuni (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/744,684

(22) PCT Filed: Jul. 27, 1999

(86) PCT No.: PCT/JP99/04028
§ 371 (c)(1),
(2), (4) Date: Jan. 29, 2001

(87) PCT Pub. No.: WO00/06659
PCT Pub. Date: Feb. 10, 2000

(30) Foreign Application Priority Data

Jul. 29, 1998 (JP) .......................................... 10-214058
Oct. 14, 1998 (JP) .......................................... 10-291971

(51) Int. Cl.$^7$ .............................................. A61L 13/02
(52) U.S. Cl. ..................... 424/448; 523/105; 523/111; 424/449
(58) Field of Search ................................ 523/105, 111, 523/61, 113; 424/448, 449

(56) References Cited

U.S. PATENT DOCUMENTS 5,296,230 A    3/1994  Chien et al.

FOREIGN PATENT DOCUMENTS

| EP | 0 328 806 A2 | 8/1989 | |
| EP | WO 92/10154 | * 6/1992 | |
| JP | A-61-12621 | 1/1986 | |
| JP | 62-209181 | 9/1987 | .............. C09J/3/14 |
| JP | A-63-104913 | 5/1988 | |
| JP | A-63-230640 | 9/1988 | |
| JP | 01-233212 | * 9/1989 | |
| JP | 1-233212 | 9/1989 | ............. A61K/9/70 |
| JP | A 1-233213 | 9/1989 | |
| JP | A 2-196714 | 8/1990 | |
| JP | A-2-233617 | 9/1990 | |
| JP | 3-39382 | 2/1991 | .......... C09J/133/08 |
| JP | A-3-220120 | 9/1991 | |
| JP | 04-266742 | * 9/1992 | |
| JP | 4-266742 | 9/1992 | ......... A61B/5/0408 |
| JP | 8-27449 | 1/1996 | .......... C09J/123/08 |
| JP | B-2604097 | 1/1997 | |
| JP | 09-143062 | * 6/1997 | |
| JP | 9-143062 | 6/1997 | ............. A61K/9/70 |
| WO | WO 92/10154 | * 6/1992 | |
| WO | WO 92/10154 A1 | 6/1992 | |
| WO | WO 93/04677 | 3/1993 | |
| WO | WO 96/08245 | 3/1996 | |

* cited by examiner

Primary Examiner—Robert D. Harlan
(74) Attorney, Agent, or Firm—Sughrue Mion, PLLC

(57) ABSTRACT

The adhesive agent composition of the present invention comprises from 50 to 90% by weight of an acrylic adhesive agent, 2.5 to 50% by weight of a polyhydric alcohol-containing liquid component, and 0.01 to 10% by weight of a salt of a mono- to tri-valence metal of an aliphatic acid that contains a hydrocarbon group of 8 to 18 carbon atoms. The adhesive agent composition shows good adhesion, cohesive force and permeability, and an adhesive drug composition having the above properties can be prepared by adding a drug (medicine, etc.) to the adhesive composition. An adhesive tape excellent in permeability or an adhesive tape preparation excellent in permeability and cutaneous absorption of the drug can be produced by coating a substrate with the adhesive agent composition or adhesive drug composition.

13 Claims, No Drawings

PRESSURE-SENSITIVE ADHESIVE COMPOSITION AND MOISTURE-PERMEABLE PRESSURE-SENSITIVE ADHESIVE TAPE, PRESSURE-SENSITIVE ADHESIVE DRUG COMPOSITION, AND PRESSURE-SENSITIVE ADHESIVE TAPE PREPARATION EACH CONTAINING THE COMPOSITION

TECHNICAL FIELD

The present invention relates to an adhesive agent composition and a permeable adhesive tape containing the adhesive agent composition, an adhesive drug composition containing the adhesive agent composition, and an adhesive tape preparation containing the adhesive drug composition.

The present invention relates in more detail to an adhesive agent composition having good adhesion to the human skin and high permeability, a permeable adhesive tape having an adhesive layer that contains the adhesive agent composition, showing firm adhesion to the skin and excellent in permeability, an adhesive drug composition containing the adhesive agent composition, and an adhesive tape preparation having an adhesive drug layer that contains the adhesive drug composition, showing firm adhesion to the skin and excellent in permeability.

BACKGROUND ART

The following materials have been actively developed: an adhesive agent composition and adhesive drug composition having good adhesion to the human skin and suitable permeability; a permeable adhesive tape having an adhesive layer that contains the adhesive agent composition; and an adhesive tape preparation having an adhesive drug layer that contains a drug, particularly a drug to be administered into a living body through the skin. Rubber-based, silicone-based, acrylic-based, vinyl acetate-based, vinyl ether-based and the like material-based adhesive agents have been used as the adhesive agents for the adhesive agent compositions and the adhesive drug compositions for the tape preparations. Of these adhesive agents, acrylic adhesive agents that show less stimulation of the skin and that are less costly are preferably used. Moreover, in order to increase the transfer to the skin of the drug in an adhesive tape preparation containing a cutaneous absorption drug, the tape preparation must be surely affixed to the skin surface. However, for an adhesive tape preparation having excessively firm adhesion strength, the corneum is sometimes peeled off to give strong stimulation of the skin when the tape preparation is peeled off the skin. In order to solve the problem, in the development of an acrylic adhesive tape preparation, the skin touch of the tape preparation should be made soft when it is allowed to adhere to the skin; moreover, in order to increase the cutaneous absorption of a drug, the adhesive agent is allowed to contain a large amount of the liquid component. For example, substances such as sorbitan esters, aliphatic esters and polyhydric alcohols are known to have the effect of promoting cutaneous absorption of drugs, and adhesive tape preparations in which the acrylic adhesive agents are allowed to contain such cutaneous absorption promoters of drugs as the above sorbitan esters have been disclosed (Japanese Unexamined Patent Publication (Kokai) Nos. 1-233212, 1-233213, 2-196714 and 2-233617). However, as a result of allowing the adhesive agent to contain such a known cutaneous absorption promoter of a drug, there arise problems as explained below. The cohesive force of the adhesive agent is lowered, and part of the adhesive layer remains, that is, retention of the adhesive layer takes place when the tape preparation is affixed to the skin and peeled off; moreover, the liquid component containing the above cutaneous absorption promoter of a drug oozes out of the adhesive layer.

Various investigations on the methods of improving the cohesive force of the acrylic adhesive agents have been carried out. One of the known methods is to subject the adhesive layer to a physical procedure such as irradiation with ultraviolet rays, an electron beam, radioactive rays or the like. These procedures such as irradiation of ultraviolet rays sometimes cause decomposition of the drug; therefore, they are not preferable ones for the adhesive agents for medical treatment.

There are other chemical procedures for improving the cohesive force of the acrylic adhesive agents. Japanese Unexamined Patent Publication (Kokai) No. 3-220120 discloses, as one of the procedures, a method of cross-linking a metal alcoholate, a metal chelate compound and/or isocyanate, etc. with a carboxyl group in an acrylic adhesive polymer. In addition to these procedures, it is known that substances such as metal salts, organic peroxides, polyurethanes and/or multifunctional compounds can be used to improve the cohesive force of the acrylic adhesive agents. However, when substances such as metal alcoholates, metal chelate compounds, isocyanates, polyurethanes and/or multifunctional compounds are used in combination with a drug having a functional group, there arise the problems that the substances and the drug mutually act to lower the cutaneous absorption of the drug, and that the adhesive agent does not show the effect of improving the cohesive force.

Furthermore, the adhesive tape preparation used for the cutaneous absorption of a drug is very excellent in administering a drug that requires continuous administration over a long period of time, an antiphlogistic antalgic that causes gastroenteropathy in oral administration, and a drug that is substantially decomposed at the initial pass in the liver. However, when the adhesive tape preparation is continuously affixed to the skin of a patient over a long period of time, there arises the problem that poisoning and itchiness of the skin appear.

In order to improve the prevention of poisoning the skin, it has heretofore been attempted to make the contents of the remaining monomers and remaining solvent as small as possible. It is fundamentally desirable to increase the permeability (dissipation of moisture) of the affixed agent and suppress the humidity (poor dissipation of moisture) of the skin in the affixed portion. However, when the sealing degree of the affixed agent is decreased by increasing the permeability, the cutaneous absorption amount of the drug is extremely decreased to create the inconvenience that achieving the initial object of the tape preparation becomes unsatisfactory. In order to keep the cutaneous absorption amount of the drug at a desired value, such a substrate having substantially no permeability or low permeability as a PET film is used in combination with a permeable adhesive layer when a nonpermeable adhesive agent is used or such an adhesive agent having permeability as an acrylic adhesive agent is used.

A so-called poultice has been known as an adhesive tape preparation causing relatively less poisoning of the skin. The poultice comprises a permeable water-containing gel adhesive layer that contains a polyacrylic acid salt or polyvinyl alcohol and a substrate showing good air permeability and stretchability such as an unwoven fabric with the adhesive layer formed on the fabric. A poultice containing, in the water-containing gel adhesive agent layer, indomethacin or ketoprofen as a medicinally effective component has been widely used as an antiphlogistic antalgic poultice in recent years. However, since the poultice shows weak adhesion to the skin, it has the following disadvantages: an auxiliary means is necessary for continuously affixing the poultice; and the gel becomes sticky when the ambient temperature rises. Therefore, an antiphlogistic antalgic tape agent has been proposed (specifications in WO 93/04677 and WO 96/08245) and practically used in place of the antiphlogistic antalgic poultice.

A rubber-based adhesive agent having a high cohesive force and high adhesion is used for the adhesive layer of such a tape preparation, and a fabric (preferably a knitted fabric) having a high stretchability is used as the substrate. As a result, the tape preparation alone can be affixed to a flexible portion such as the cubitus of a patient, and the affixed state can be maintained.

However, the rubber-based adhesive agent substantially has no permeability. Therefore, the cutaneous absorption of a drug of the tape preparation is improved at the cost of the permeability. Moreover, in general, a relatively low molecular weight chemical substance such as a tackifier must be added to the rubber-based adhesive agent. Such an additive is considered to be a main cause of poisoning of the skin.

Such adhesive agents having a strong cohesive force and sufficient adhesion to the skin as a silicone-based, an acrylic, a vinyl acetate-based and vinyl ether-based adhesive agent are generally used for the adhesive layer of the tape preparation in addition to the rubber-based adhesion agent. Of these adhesive agents, the acrylic adhesive agent that does not require addition of an antioxidant and a tackifier is preferably used. However, a polyester film or the like substantially having no permeability is used as the substrate for the tape preparation to improve the cutaneous absorption of the drug at the cost of the moisture dissipation of the skin.

Furthermore, a sorbitan ester is known to have the effect of promoting cutaneous absorption of a drug, and a poultice and a cream agent in which an alcohol and a sorbitan ester are used in combination have been proposed (Japanese Unexamined Patent Publication (Kokai) No. 61-12621, Japanese Patent Publication No. 2604097, Japanese Unexamined Patent Publication (Kokai) No. 63-104913 and Japanese Unexamined Patent Publication (Kokai) No. 63-230640). Moreover, a tape preparation in which an acrylic adhesive agent is allowed to contain a sorbitan ester has also been disclosed (Japanese Unexamined Patent Publication (Kokai) Nos. 1-233212, 1-233213, 2-196714 and 2-233617). However, a nonpermeable polyethylene terephthalate film or the like has been used as the substrates of these known tape preparations, and permeability necessary for the preparations is not ensured. It is clear from the explanation above that a tape preparation containing an oily adhesive agent composition showing high permeability, high cutaneous absorbability and high cohesive force has not been known.

DISCLOSURE OF THE INVENTION

An object of the present invention is to provide: an adhesive agent composition which has firm adhesion to the human skin, high cohesive force, suitable permeability and practically adequate medicinal adaptability to a cutaneously absorbable drug and which shows no stimulation or extremely little stimulation of the human skin; a permeable adhesive tape which has an adhesive layer containing the adhesive agent composition and consequently showing high cohesive force, which produces no or an extremely decreased partial retention of the adhesive layer and which has high permeability; an adhesive drug composition which contains the adhesive agent composition and a drug, particularly a cutaneously absorbable drug; and an adhesive tape preparation which has a drug adhesive layer containing the adhesive drug composition and having high cohesive force, which produces no or an extremely decreased partial retention of the adhesive layer and which has high permeability.

The object is achieved by the invention described below.

An adhesive agent composition of the present invention comprises 50 to 90% by weight of an acrylic adhesive agent, 2.5 to 50% by weight of a polyhydric alcohol-containing liquid component, and 0.01 to 10% by weight of an aliphatic acid metal salt formed from an aliphatic acid that has a hydrocarbon group containing from 8 to 18 carbon atoms and a mono- to tri-valence metal.

A permeable adhesive tape of the present invention comprises a substrate and an adhesive layer formed on one side of the substrate and containing the adhesive agent composition of the invention.

An adhesive drug composition of the present invention comprises the adhesive agent composition of the invention and 0.05 to 40% by weight of a drug based on the weight of the adhesive agent composition.

An adhesive tape preparation of the present invention comprises a substrate and an adhesive drug layer formed on one side of the substrate and containing the adhesive drug composition of the invention.

BEST MODE FOR CARRYING OUT THE INVENTION

The adhesive agent composition of the present invention comprises 50 to 90 parts by weight of an acrylic adhesive agent, 2.5 to 50 parts by weight of a polyhydric alcohol-containing liquid component, 0.01 to 10 parts by weight of an aliphatic acid metal salt formed from an aliphatic acid that has a hydrocarbon group of 8 to 15 carbon atoms and a mono- to tri-valence metal.

The acrylic adhesive agent preferably contains at least one polymer selected from the group consisting of homopolymers of acrylic acid, methacrylic acid, an alkyl acrylate and an alkyl methacrylate, and copolymers containing at least one of the above monomer components. In the above copolymers, examples of an ethylene type unsaturated comonomer that copolymerizes with at least one monomer selected from the group consisting of acrylic acid, methacrylic acid, an alkyl acrylate and an alkyl methacrylate preferably include: hydroxyl group-containing monomers such as vinyl alcohol, 2-hydroxy(meth)acrylate and hydroxypropyl (meth)acrylate; carboxyl group-containing monomers such as (meth)acrylic acid, itaconic acid, crotonic acid, maleic acid, maleic anhydride and fumaric acid; sulfoxyl group-containing monomers such as styrenesulfonic acid, allylsulfonic acid, sulfopropyl acrylate, (meth) acryloyloxynaphthenesulfonic acid, (meth) acrylamidomethylpropanesulfonic acid and acryloyloxybenzenesulfonic acid; amino group-containing monomers such as dimethylaminoethyl acrylate and vinylpyrrolidone; hydroxyl group-containing monomers such as hydroxyethyl (meth)acrylate and hydroxypropyl (meth)acrylate; amide group-containing acrylic monomers such as (meth) acrylamide, dimethyl(meth)acrylamide, N-butyl(meth) acrylamide, tetramethylbutyl(meth)acrylamide, N-methylol (meth)acrylamide and ethoxymethyl(meth)acrylamide; alkylaminoalkyl group-containing acrylic monomers such as aminoethyl (meth)acrylate, dimethylaminoethyl (meth) acrylate, diethylaminoethyl (meth)acrylate and tert-butyl (meth)acrylate; alkoxy group- (or ether bond-) containing monomers (the ether bond being in the side chain) such as methoxyethyl (meth)acrylate, ethoxyethyl (meth)acrylate, butoxyethyl (meth)acrylate, tetrahydrofurfuryl (meth) acrylate, methoxyethylene glycol (meth)acrylate, methoxydiethylene glycol (meth)acrylate, methoxypolyethylene glycol (meth)acrylate and methoxypolypropylene glycol (meth) acrylate; saccharide chain-containing monomers such as glycosyloxyethyl (meth)acrylate, galactosyloxyethyl (meth) acrylate, manosyloxyethyl (meth)acrylate and trehalosyloxyethyl (meth)acrylate; vinyl-based monomers such as N-(meth)acryloylamino acid; acrylic monomers such as a urethane ester of acrylic acid, a urea ester and an isocyanate ester; and vinyl-based monomers such as (meth) acrylonitrile, vinyl acetate, vinyl propionate, vinyl chloride, vinylpyrrolidone, vinylpyridine, vinylpyrazine, vinylpiperazine, vinylpiperidone, vinylpyrimidine, vinylpyrrole, vinylimidazole, vinylcaprolactam, vinyloxazole, vinylthiazole, vinylmorpholine, styrene, α-methylstyrene and bis(N,N-dimethylaminoethyl) maleate. These comonomers are copolymerized in the acrylic copolymers preferably in a content of 2 to 60% by weight, more preferably 5 to 50% by weight. When the content of the comonomers fall outside the above range, acrylic copolymers showing a satisfactory adhesive strength and a satisfactory cohesive force sometimes cannot be obtained.

Furthermore, the adhesive agent contained in the adhesive agent composition of the present invention is preferably variously selected in accordance with the type of the drug mixed with the adhesive agent so that the drug is decomposed as little as possible. In general, the mixing amount of the acrylic adhesive agent in the adhesive agent composition, particularly in the drug composition can be decreased by using a copolymer with a comonomer having such a reactive functional group which is generally considered to be highly reactive as a carboxyl group, an amino group or an acid amide group. Moreover, masking the reactive functional group can lower the reactivity of the copolymer.

The adhesive agent composition of the present invention contains the acrylic adhesive agent in a content of 50 to 90% by weight, preferably 70 to 90% by weight.

When the content of the acrylic adhesive agent is less than 50% by weight, the cohesive force of the adhesive agent composition thus obtained inconveniently becomes insufficient. When the content exceeds 90% by weight, the adhesive agent composition thus obtained becomes viscous, and affixing the adhesive tape thus obtained to a patient inconveniently gives an unpleasant feeling.

The adhesive agent composition of the present invention contains a polyhydric alcohol-containing liquid component. The polyhydric alcohol-containing liquid component contains at least one polyhydric alcohol. The content is preferably from 1 to 30% by weight, more preferably from 7.5 to 20% by weight based on the weight of the entire adhesive agent composition.

Preferred examples of the polyhydric alcohol contained in the polyhydric alcohol-containing liquid component include glycerin, propylene glycol, 1,3-butylene glycol, diglycerin, dipropylene glycol, 1,2,6-hexanetriol, sorbitol polyethylene glycol and pentaerythritol. These polyhydric alcohols show the effect of enhancing the effect of an aliphatic acid metal salt added to the adhesive agent composition of the present invention as an improver of the cohesive force. The content of the polyhydric alcohol is preferably from 7.5 to 50% by weight based on the weight of the adhesive agent composition. When the content of the polyhydric alcohol is less than 7.5% by weight, the cutaneous absorption of a drug that is incorporated into the adhesive agent composition thus obtained sometimes becomes insufficient. When the content exceeds 50% by weight, the cohesive force of the adhesive agent composition sometimes become insufficient. As a result, the adhesive agent layer sometimes remains on the skin when the tape preparation is peeled off.

The above polyhydric alcohol-containing liquid component may contain at least one substance selected from the group consisting of sorbitan esters, aliphatic esters other than the sorbitan esters, and polyvinylpyrrolidone, in addition to the above polyhydric alcohols. Sorbitan esters, aliphatic esters different from the sorbitan esters, and polyvinylpyrrolidone in combination with the polyhydric alcohols act to promote cutaneous absorption of the drug contained in the adhesive agent composition or drug composition.

Sorbitan esters used in the present invention are preferably selected from sorbitan esters and poly(oxyalkylene) sorbitan esters of an aliphatic acid having a hydrocarbon group of 12 to 18 carbon atoms.

Sorbitan esters used in the present invention are selected from, for example, sorbitan monolaurate, sorbitan monopalmitate, sorbitan monostearate, sorbitan monooleate, sorbitan trioleate, poly(oxyethylene)sorbitan monolaurate, poly(oxyethylene)sorbitan monopalmitate, poly (oxyethylene)sorbitan monostearate, poly(oxyethylene) sorbitan monooleate, poly(oxyethylene)sorbitan trioleate and the like. Of these sorbitan esters, sorbitan monolaurate, sorbitan monooleate, sorbitan trioleate, poly(oxyethylene)

sorbitan monolaurate, poly(oxyethylene)sorbitan monopalmitate and poly(oxyethylene)sorbitan monostearate are preferably used for cutaneous absorption tape preparations that show high drug permeability under a high permeability condition.

The content of a sorbitan ester in the polyhydric alcohol-containing liquid component is preferably from 0.5 to 20% by weight, more preferably from 1 to 10% by weight based on the weight of the entire adhesive agent composition when the content of the sorbitan ester is less than 0.5% by weight and the adhesive agent composition contains a drug, the effect of improving cutaneous absorption of the drug becomes inadequate. When the content exceeds 20% by weight, the adhesive agent composition thus obtained shows insufficient self-cohesive force, and part of the adhesive layer sometimes remains on the skin after peeling the adhesive tape or tape preparation off the skin.

Aliphatic esters (different from the sorbitan esters) contained in the polyhydric alcohol-containing liquid component are preferably selected from isopropyl myristate, isopropyl palmitate, isooctyl palmitate, ethyl oleate and diethyl sebacate and the like. Of these aliphatic esters, isopropyl myristate and/or isooctyl palmitate is preferably used. The content of such a higher aliphatic ester is preferably from 1 to 30% by weight, more preferably from 5 to 20% by weight based on the weight of the entire adhesive agent composition. When the content of an aliphatic ester is less than 1% by weight and the adhesive agent composition contains a drug, the effect of improving cutaneous absorption of the drug sometimes becomes inadequate. When the content exceeds 30% by weight, the adhesive agent composition shows an insufficient self-agglomerating capacity, and part of the adhesive agent layer sometimes remains on the skin after peeling the adhesive tape preparation off the skin.

When the polyhydric alcohol-containing liquid component contains polyvinylpyrrolidone, the content is preferably from 3 to 20% by weight, more preferably from 5 to 10% by weight based on the weight of the entire composition when the content exceeds 20% by weight, the adhesive agent composition thus obtained shows an insufficient self-agglomerating capacity, and part of the adhesive layer sometimes remains on the skin after peeling the adhesive tape or adhesive tape preparation off the skin. When the content is less than 3% by weight and the adhesive agent composition thus obtained contains a drug, the effect of improving cutaneous absorption of the drug sometimes becomes inadequate.

In the polyhydric alcohol-containing liquid component used in the present invention, combined use of a sorbitan ester and an aliphatic ester different from the sorbitan ester and/or polyvinylpyrrolidone, in particular, use of an aliphatic ester in combination can more enhance the cutaneous absorbability of a drug contained in the adhesive agent composition. The total content of the sorbitan ester, and the aliphatic ester and/or polyvinylpyrrolidone used in combination therewith is then preferably from 10 to 40% by weight based on the weight of the entire adhesive agent composition.

The adhesive agent composition of the present invention contains an aliphatic acid metal salt formed from an aliphatic acid having a hydrocarbon group of 8 to 18 carbon atoms and a mono- to tri-valence metal. The aliphatic acid metal salt is effective in enhancing the cohesive force of the adhesive agent composition. Preferably, a salt of an aliphatic acid of 8 to 18 carbon atoms, for example, an aliphatic acid selected from caprilic acid, lauric acid, myristic acid, stearic acid and oleic acid with a metal selected from an alkali metal (e.g., sodium), an alkaline earth metal (e.g., magnesium), zinc and aluminum is employed.

The aliphatic acid metal salt used in the present invention is selected from, for example, sodium caprylate, sodium laurate, sodium myristate, sodium stearate, sodium oleate, magnesium stearate, zinc stearate, aluminum stearate and the like. Moreover, use of the aliphatic acid metal salt in combination with the above polyhydric alcohol can further improve the cohesive force of the adhesive agent composition. The mixing amount of the aliphatic acid metal salt is preferably from 0.01 to 10% by weight, more preferably from 0.1 to 5% by weight based on the weight of the entire adhesive composition. When the content of the aliphatic acid metal salt is less than 0.1% by weight, the adhesive agent composition thus obtained shows an insufficient cohesive force. Moreover, when the content is at least 10% by weight, excessive gelation takes place in the adhesive agent composition thus obtained, and handling of the composition becomes difficult. Furthermore, when a drug is incorporated into the adhesive agent composition, the aliphatic acid metal salt does not influence the cutaneous absorption of the drug.

The permeable adhesive tape of the present invention is prepared by forming an adhesive layer containing the adhesive agent composition of the present invention on one side of a substrate.

The substrate used for the permeable adhesive tape of the present invention preferably has air permeability and permeability; however, it preferably permits no transfer (transmission, diffusion, etc.) of a chemical drug, particularly no transfer of a medicine. The following materials can be used as a substrate that prevents a drug from transferring: a plastic film or porous film composed of polyethylene-based, polypropylene-based, polyester-based, polyamide-based, polytetrafluoroethylene-based, polyvinyl chloride-based or polyurethane-based polymer; and an unwoven fabric, a knitted fabric or a woven fabric prepared from a fiber formed from any of these polymers. The above porous film, or the above unwoven fabric, knitted fabric or woven fabric has good air permeability, permeability and flexibility, and is a substrate effective in preventing stimulation of the skin.

The permeability of the adhesive tape of the present invention is preferably at least 300 $g/m^2 \cdot day$, more preferably from 600 to 800 $g/m^2 \cdot day$.

The adhesive layer of the adhesive tape of the present invention preferably has a thickness of 5 to 1,000 $\mu m$, more preferably 10 to 500 $\mu m$.

The adhesive tape of the present invention can be produced by forming an adhesive layer containing the adhesive agent composition of the present invention on one side of the substrate by hot melt coating, emulsion coating or solvent coating. Of these coating methods, the solvent coating method is preferably used. The solvent coating method is conducted in the following manner: an adhesive agent composition is dissolved in a low boiling point solvent (preferably having a boiling point up to 80° C.) such as ethyl acetate to give a dope for coating, and a substrate is coated with the dope on one side and dried to form an adhesive layer; alternatively, a releasing material is coated with the dope on one side, and the coating layer is dried, followed by joining the coating adhesive layer on the releasing material to the substrate.

Examples of the solvent used for the preparation of the dope include ethyl acetate, chloroform, methylene chloride, cyclohexane and tetrahydrofuran. Of these solvents, ethyl acetate is preferably used. Moreover, a solvent mixture of ethyl acetate and alcohol is preferably used because it prevents gelation of when an aliphatic acid metal salt is added.

Moreover, examples of the releasing material include a metal foil coated with a release agent such as silicone and fluorine, and a film of plastics such as polyester, polyolefin, cellulose ester and polyamide. The releasing material is used to protect the adhesive layer surface of the adhesive tape until the tape is used.

The adhesive drug composition of the present invention contains the above adhesive agent composition of the present invention and a drug in an amount of 0.05 to 40% by weight, preferably 5 to 10% by weight based on the weight of the adhesive agent composition. When the content of the drug is less than 0.05% by weight, the drug composition thus obtained cannot show the desired effect of the added drug. Moreover, when the content of the drug exceeds 40% by weight, the drug composition thus obtained shows insufficient adhesion.

Drugs used for the adhesive drug composition include one or more pharmacologically active substances such as nonsteroidal anti-flammatory agents, antihypertensives, local anesthetics, antibiotics, calcium antagonists, cardiotonics, antiepileptics, hypotensive diuretics, antifungals, antiallergics-antihistaminics, anti-cancer agents, antipsychotropics, antivertigo agents, sleep controlling agents, coronary vasodilators, hormones, hypotensors, treating agents for asthma and nositis, hypoglycemics and antiulcer agents.

Typical examples of the drugs are shown below.

1) Nonsteroidal anti-flammatory agents including acetylsalicylic acid, methyl salicylate, indomethacin, diclofenac, ibuprofen, ketoprofen, flurbiprofen, mefenamic acid, phenylbutazone, aminopyrin, piroxicam and felbinac.

2) Antihypertensives including pindolol, atenolol, propanolol, nadolol, ajmaline, alprenolol hydrochloride, metoprolol tartrate, quinidine sulfate, timolol maleate and disopyramide.

3) Local anesthetics including tetracaine, procaine, benzocaine and lidocaine.

4) Antibiotics including chloramphenicol and tetracycline.

5) Calcium antagonists including nifedipine and nicardipine.

6) Cardiotonics including dopamine hydrochloride and digitalis.

7) Antiepileptics including sodium valproate and phenytoin.

8) Hypotensive diuretics including hydrochlorothiazide.

9) Antifungals including griseofulvin and amphotericin B.

10) Antiallergics-antihistaminics including cycloheptadine hydrochloride, diphenhydramine hydrochloride, mequitazine and phenbenzamine.

11) Anti-cancer agents including 5-fluorouracil and mitomycin C.

12) Antipsychotropics including etizolam, maprotiline hydrochloride, amitriptyline hydrochloride, mianserin hydrochloride and diazepam.

13) Antivertigo agents including scopolamine.

14) Sleep controlling agents including amobarbital and phenobarbital.

15) Coronary vasodilators including dipyridamor, diltiazem, isosorbide nitrate, nifedipine, nitroglycerin and pentaerythritol tetranitrate.

16) Hormones including estradiol, estrogen, testosterone, progesterone and prostaglandin.

17) Hypotensors including clonidine hydrochloride, plazosin hydrochloride, guanfacine hydrochloride, bunazosin hydrochloride, arotinolol hydrochloride, bunitorolol hydrochloride, penbutolol sulfate, guanabenz acetate and eranapuril maleate 18) Treating agents for asthma and nositis including azelastin hydrochloride, cromoglicic acid and ketotifen fumarate.

19) Hypoglycemics including gliclazide and glibenclamid.

20) Antiulcer agents including glycopyrronium bromide, famotidine and clebopride malate.

At least two of the above drugs can be used in combination in accordance with the object and action of the medicinal treatment.

For the adhesive drug composition of the present invention, the cohesive force of the composition can be improved without lowering the cutaneous absorbability of the drug by using an adhesive agent composition in which the polyhydric alcohol-containing liquid component and aliphatic acid metal salt are mixed with the acrylic adhesive agent.

The adhesive tape preparation of the present invention is produced by forming an adhesive drug layer containing the adhesive drug composition of the present invention on one side of a substrate.

The substrate of the adhesive tape preparation of the present invention can be selected from a material similar to the substrate of the permeable adhesive tape in the present invention. Moreover, the adhesive drug layer can be formed from the adhesive drug composition of the present invention in the same manner as in the formation of the adhesive layer in the production of the permeable adhesive tape.

For the adhesive tape preparation of the present invention, the permeability is preferably at least 300 g/$m^2$·day, more preferably from 600 to 800 g/$m^2$·day.

Furthermore, for the adhesive tape preparation of the present invention, the thickness of the adhesive drug layer is preferably from 5 to 1,000 μm, more preferably from 10 to 500 μm. The adhesive drug layer in the adhesive tape preparation of the present invention contains the adhesive composition of the present invention in combination with a drug. As a result, the adhesive drug layer can show good cutaneous absorption of the drug as well as good air permeability and permeability.

EXAMPLES

The present invention will be further explained below by making reference to examples. In the examples, the cutaneous absorption test of a drug in an adhesive tape preparation, the cohesive force test, peeling test and permeability measurement test of an adhesive layer or adhesive drug layer were conducted by the following procedures.

(1) Cutaneous Absorption Test of Drugs

Back skin of a YMP (Yucatan Micro Pig: female, 20 kg) to which a dermal external drug composition (0.4 $cm^2 \times 0.4$ $cm^2$) was affixed was mounted on the upper portion of a vertical diffusion cell. In the lower portion of the cell was placed 10 ml of a phosphoric acid buffer (pH=7.4, containing 1% of sodium dodecylsulfate when estradiol was used), and stirred for 24 hours (48 hours when estradiol was used). The phosphoric acid buffer was sampled from the lower portion of the cell after stirring, and the concentration of the drug transferred to the buffer in the lower portion of the cell was quantitatively determined by liquid chromatography.

(2) Cohesive Force Test

The adhesive layer or adhesive drug layer of an adhesive tape or adhesive tape preparation containing a sample adhesive agent composition or adhesive drug composition was affixed to a Bakelite plate. The tape was then peeled off, and the presence of absence of the adhesive layer or adhesive drug layer on the Bakelite plate surface was visually judged in accordance with the following criteria: good (no adhesion retention of the adhesive layer or adhesive drug layer); and poor (adhesion retention thereof).

(3) Peeling Test

The adhesive layer of a sample adhesive tape 12 mm wide or the adhesive drug layer of a sample adhesive tape preparation 12 mm wide was affixed to a Bakelite plate surface. A load of 300 $g/cm^2$ was applied to the tape or of tape preparation to allow it to adhere thereto. One end of the sample adhesive tape or adhesive tape preparation was then peeled off the plate at a peeling rate of 300 mm/min at a peel angle of 180°, and the peeling strength was measured.

(4) Permeability Test

In a glass weighing bottle having an inside diameter of 38 mm was placed 26 g of calcium chloride. An adhesive layer, an adhesive drug layer or a support allowed to adhere to a gauze having a permeability of 11,000 $g/m^2 \cdot day$ was then fixed to the upper portion of the bottle. The bottle was then left in a thermo-hygrostat at 40° C. at a relative humidity of 70% for 3 hours. The moisture content permeated through the specimen per square meter per 24 hours was calculated from the increased mass of the contents of the test weighing bottle. The permeability of the adhesive layer, adhesive drug layer or support was represented by the measured value thus obtained.

Materials used in the examples will be described below.

(1) Ketoprofen and felbinac used in the present examples were obtained from Sigma Chemical. Estradiol and testosterone were obtained from TOKYO KASEI ORGANIC CHEMICAL. All the following compounds were obtained from Kanto Chemical Co., Inc.: glycerin (GC), 1,2,6-hexanetriol, isopropyl myristate (IPM), isooctyl palmitate (IOP), ethyl oleate (OE), magnesium stearate (StMg), sorbitan monolaurate (SPAN20), sorbitan monooleate (SPAN80), sorbitan trioleate (SPAN85), poly(oxyethylene) sorbitan monolaurate (TWEEN20), poly(oxyethylene) sorbitan monopalmitate (TWEEN40), poly(oxyethylene) sorbitan monostearate (TWEEN60) and polyvinylpyrrolidone (PVP).

(2) The pig skin used in the permeation experiment was obtained from Charles River.

(3) A permeable woven fabric composed of polyethylene terephthalate was used as the substrate. MOHRUS TAPE (trade name, manufactured by Hisamitsu Pharmaceutical Co. Inc.) and Cell Touch (trade name, manufactured by Takeda Chemical Industries Ltd.) were used as reference samples. MOHRUS TAPE was a tape preparation having an adhesive layer which contains ketoprofen as a drug and for which a rubber-based adhesive agent was used, and showing no permeability. Moreover, Cell Touch was a poultice containing felbinac as a drug.

Two polyhydric alcohols were used in Examples 1, 2 to be explained below, and the cohesive force was examined. Systems in which an aliphatic acid metal salt was used or no polyhydric alcohol was used were selected in Comparative Examples 1 to 6. MOHRUS TAPE was used in Reference Example 1, and the results were compared and examined.

Example 1

To 9.3 g of an acrylic adhesive agent (an acrylic adhesive agent obtained by copolymerizing the three components composed of 7% by weight of methyl acrylate, 90% by weight of 2-ethylhexyl acrylate and 3% by weight of acrylic acid; a dope-like material prepared by dissolving the adhesive agent in ethyl acetate and containing 21.6% of the agent was used) were added 2.0 g of glycerin and 0.04 g of magnesium stearate; an ethyl acetate-ethanol mixture solution (ethyl acetate/ethanol volume ratio of 2/1) was further added in an amount of 45 ml. The mixture was stirred with a homogenizer to give a coating liquid for an adhesive layer. A PET film treated with silicone was coated with the coating liquid by a doctor knife to form a coating layer (50 μm thick after drying), which was dried at 60° C. for 30 minutes to form an adhesive layer 50 μm thick. The adhesive tape thus obtained was used in the cohesive force test and peeling test. The adhesive layer of the adhesive tape contained 49% by weight of the acrylic adhesive agent, 50% by weight of glycerin and 1% by weight of magnesium stearate. Table 1 shows the test results.

Example 2

An adhesive tape was produced in the same manner as in Example 1 except that 1,2,6-hexanetriol was used in place of glycerin.

Table 1 shows the test results.

Comparative Example 1

An adhesive tape was produced in the same manner as in Example 1 except that the adhesive agent composition (coating liquid) was prepared in such a manner that the adhesive layer obtained after drying comprised 50% by weight of an acrylic adhesive agent and 50% by weight of glycerin.

Table 1 shows the test results.

Comparative Example 2

An adhesive tape was produced in the same manner as in Example 1 except that the adhesive agent composition (coating liquid) was prepared in such a manner that the adhesive layer thus obtained comprised 49.95% by weight of an acrylic adhesive agent, 50% by weight of glycerin and 0.05% by weight of magnesium stearate.

Table 1 shows the test results.

Comparative Example 3

An adhesive tape was produced in the same manner as in Example 1 except that the adhesive agent composition (coating liquid) was prepared in such a manner that the adhesive layer thus obtained comprised 45% by weight of an acrylic adhesive agent, 50% by weight of glycerin and 5% by weight of magnesium stearate.

Table 1 shows the test results.

Comparative Example 4

An adhesive tape was produced in the same manner as in Example 1 except that the adhesive composition (coating liquid) was prepared in such a manner that the adhesive layer thus obtained comprised 49% by weight of an acrylic adhesive agent, 50% by weight of isopropyl myristate and 1% by weight of magnesium stearate.

Table 1 shows the test results.

Comparative Example 5

An adhesive tape was produced in the same manner as in Comparative Example 4 except that isooctyl palmitate was used in place of isopropyl myristate.

Table 1 shows the test results.

Comparative Example 6

An adhesive tape was produced in the same manner as in Comparative Example 4 except that oleic acid was used in place of isopropyl myristate.

Table 1 shows the test results.

Reference Example 1

MOHRUS TAPE was used in the same tests as in Example 1.

Table 1 shows the test results.

TABLE 1

| | Adhesive agent composition | | | Cohesive force of an adhesive layer (prevention of adhesion retention of adhesive drug layer) | Peeling strength (gf) |
|---|---|---|---|---|---|
| | Acrylic adhesive agent (wt. %) | Polyhydric alcohol-containing liquid component (wt. %) | Aliphatic acid salt (wt. %) | | |
| Ex. 1 | 49 | GC 50 | StMg 1 | good | $2.22 \times 10^2$ |
| Ex. 2 | 49 | 1,2,6-hexanetriol 50 | StMg 1 | good | $2.38 \times 10^2$ |
| Comp. Ex. 1 | 50 | GC 50 | — | poor | — |
| Comp. Ex. 2 | 49.95 | GC 50 | StMg 0.05 | poor | — |
| Comp. Ex. 3 | 45 | GC 50 | StMg 5 | coating being impossible | — |
| Comp. Ex. 4 | 49 | IPM 50 | StMg 1 | poor | — |
| Comp. Ex. 5 | 49 | IOP 50 | StMg 1 | poor | — |
| Comp. Ex. 6 | 49 | OA 50 | StMg 1 | poor | — |
| Ref. Ex. 1 | — | — | — | good | $1.98 \times 10^2$ |

Note:
GC = glycerin
StMg = magnesium stearate
IPM = isopropyl myristate
IOP = isooctyl palmitate
OA = oleic acid
Coating being impossible = Gelation of the coating liquid took place, and conducting coating was impossible because handling became impossible during preparation of the adhesive agent.

In Examples 3 to 8, adhesive agents containing ketoprofen as a pharmacologically active substance were used, and the effects of six aliphatic acid metal salts on the improvement of the cohesive force were investigated. Moreover, aliphatic esters were added as liquid components in Examples 9, 10 in addition to a polyhydric alcohol, and their influence on the cohesive force was investigated. In comparative Examples 7, 8, investigations were carried out on a system in which either an aliphatic acid metal salt or a polyhydric alcohol was not used, and a system in which ethyl acetoacetate aluminum diisopropionate was used.

Example 3

An adhesive tape was produced in the same manner as in Example 1 except that the adhesive layer subsequent to drying was an adhesive drug layer composed of an adhesive drug composition comprising 43% by weight of the acrylic adhesive agent, 50% by weight of glycerin, 1% by weight of magnesium stearate and 6% by weight of ketoprofen. An adhesive tape preparation was thus obtained.

Table 2 shows the test results.

Example 4

An adhesive tape preparation was produced in the same manner as in Example 3 except that sodium caprylate was used in place of magnesium stearate.

Table 2 shows the test results.

Example 5

An adhesive tape preparation was produced in the same manner as in Example 3 except that sodium laurate was used in place of magnesium stearate.

Table 2 shows the test results.

Example 6

An adhesive tape preparation was produced in the same manner as in Example 3 except that sodium stearate was used in place of magnesium stearate.

Table 2 shows the test results.

Example 7

An adhesive tape preparation was produced in the same manner as in Example 3 except that zinc stearate was used in place of magnesium stearate.

Table 2 shows the test results.

Example 8

An adhesive tape preparation was produced in the same manner as in Example 3 except that aluminum stearate was used in place of magnesium stearate.

Table 2 shows the test results.

Example 9

An adhesive tape was produced in the same manner as in Example 1 except that the adhesive layer subsequent to drying was an adhesive drug layer composed of an adhesive drug composition comprising 43% by weight of the acrylic adhesive agent, 10% by weight of sorbitan monolaurate, 40% by weight of glycerin, 1% by weight of magnesium stearate and 6% by weight of ketoprofen to give an adhesive tape preparation.

Table 2 shows the test results.

Example 10

An adhesive tape was produced in the same manner as in Example 1 except that the adhesive layer subsequent to drying was an adhesive drug layer composed of an adhesive drug composition comprising 43% by weight of the acrylic adhesive agent, 10% by weight of sorbitan monolaurate, 20% by weight of isopropyl myristate, 20% by weight of glycerin, 1% by weight of magnesium stearate and 6% by weight of ketoprofen to give an adhesive tape preparation.

Table 2 shows the test results.

Comparative Example 7

An adhesive tape preparation was produced in the same manner as in Example 3 except that isopropyl myristate was used in place of glycerin.

Table 2 shows the test results.

Comparative Example 8

An adhesive tape preparation was produced in the same manner as in Example 3 except that sorbitan monolaurate was used in place of glycerin.

Table 2 shows the test results.

Comparative Example 9

An adhesive tape preparation was produced in the same manner as in Example 3 except that magnesium stearate was not used.

Table 2 shows the test results.

Comparative Example 10

An adhesive tape preparation was produced in the same manner as in Example 3 except that ethyl acetoacetate aluminum diisopropionate was used in place of magnesium stearate.

Table 2 shows the test results.

TABLE 2

| | Composition of adhesive drug layer | | | | Cohesive force (prevention of adhesion retention of adhesive drug layer) | Peeling strength (gf) |
|---|---|---|---|---|---|---|
| | Acrylic adhesive agent (wt. %) | Polyhydric alcohol-containing liquid component (wt. %) | Aliphatic acid salt (wt. %) | Drug (wt. %) | | |
| Ex. 3 | 43 | GC 50 | StMg 1 | KP 6 | good | $2.42 \times 10^2$ |
| Ex. 4 | 43 | GC 50 | CpNa 1 | KP 6 | good | $2.37 \times 10^2$ |
| Ex. 5 | 43 | GC 50 | RuNa 1 | KP 6 | good | $2.22 \times 10^2$ |
| Ex. 6 | 43 | GC 50 | StNa 1 | KP 6 | good | $2.51 \times 10^2$ |
| Ex. 7 | 43 | GC 50 | StZn 1 | KP 6 | good | $2.87 \times 10^2$ |
| Ex. 8 | 43 | GC 50 | StAl 1 | KP 6 | good | $2.61 \times 10^2$ |
| Ex. 9 | 43 | SPAN20 10 GC 40 | StMg 1 | KP 6 | good | $2.73 \times 10^2$ |
| Ex. 10 | 43 | SPAN20 10 IPM 50 GC 20 | StMg 1 | KP 6 | good | $2.69 \times 10^2$ |
| Comp. Ex. 7 | 43 | IPM 50 | StMg 1 | KP 6 | poor | — |
| Comp. Ex. 8 | 43 | SPAN20 50 | StMg 1 | KP 6 | poor | — |
| Comp. Ex. 9 | 44 | GC 50 | — | KP 6 | poor | — |
| Comp. Ex. 10 | 43 | GC 50 | Al 1 | KP 6 | poor | — |

Note:
GC = glycerin
SPAN20 = sorbitan monolaurate
IPM = isopropyl myristate
StMg = magnesium stearate
CpNa = sodium caprylate
RuNa = sodium laurate
StNa = sodium stearate
StZn = zinc stearate
StAl = aluminum stearate
Al = ethyl acetoacetate aluminum diisopropionate
KP = ketoprofen The influence of an aliphatic acid metal salt on the cutaneous permeability of a drug was investigated in Example 11. The cutaneous permeability of a drug was investigated in a system without an aliphatic acid metal salt and in a system in which ethyl acetate aluminum diisopropionate was used as a metal chelate compound that has the possibility of showing a mutual action with the drug, in Comparative Examples 11, 12.

Example 11

To 15.3 g of an acrylic adhesive agent (an acrylic adhesive agent obtained by copolymerizing the three components composed of 7% by weight of methyl methacrylate, 90% by weight of 2-ethylhexyl acrylate and 3% by weight of acrylic acid; a dope-like material prepared by dissolving the adhesive agent in ethyl acetate and containing 21.6% of the agent was used) were added 0.1 g of sorbitan monolaurate, 0.3 g of glycerin, 0.24 g of ketoprofen and 0.04 g of magnesium stearate; an ethyl acetate-ethanol solution mixture (ethyl acetate/ethanol volume ratio of 2/1) was further added in an amount of 45 ml. The mixture was stirred with a homogenizer to give a coating liquid for an adhesive drug layer of an adhesive tape preparation.

A PET film treated with silicone was coated with the coating liquid by a doctor knife to form a coating layer (50 μm thick after drying), which was dried at 60° C. for 30 minutes to form an adhesive drug layer 50 μm thick. The adhesive drug layer was affixed to an air permeable woven fabric composed of polyethylene terephthalate fiber, and subjected to the permeability test.

Table 3 shows the test results.

Comparative Example 11

An adhesive tape preparation was produced in the same manner as in Example 11 except that magnesium stearate was not used.

Table 3 shows the test results.

Comparative Example 12

An adhesive tape preparation was produced in the same manner as in Example 11 except that ethyl acetate aluminum diisopropionate was used in place of magnesium stearate.

Table 3 shows the test results.

TABLE 3

| | Composition of adhesive drug layer | | | | Cohesive force (prevention of adhesion retention of adhesive drug layer) | Cutaneous absorption amount of ketoprofen (mg/cm² · 24 hr) |
|---|---|---|---|---|---|---|
| | Acrylic adhesive agent (wt. %) | Polyhydric alcohol-containing liquid component (wt. %) | Aliphatic acid salt (wt. %) | Drug (wt. %) | | |
| Ex. 11 | 83 | SPAN20 2.5 GC 7.5 | StMg 1 | KP 6 | good | 60 |
| Comp. Ex. 11 | 84 | SPAN20 2.5 GC 7.5 | — | KP 6 | poor | 57 |
| Comp. Ex. 12 | 83 | SPAN20 2.5 GC 7.5 | Al 1 | KP 6 | poor | 21 |

Note:
SPAN20 = sorbitan monolaurate
GC = glycerin
StMg = magnesium stearate
Al = ethyl acetoacetate aluminum diisopropionate
KP = ketoprofen It has been confirmed from Table 3 that an aliphatic acid metal salt contained in an adhesive drug layer has the effect of improving the cohesive force of the adhesive drug layer without decreasing the cutaneous absorption of a drug.

In Examples 12 to 17 to be explained below, investigations on the absorption promoting effect of six absorbefacients and the cohesive force and permeability of adhesive agents containing the absorbefacients were carried out. In Comparative Examples 13 to 18, experiments were conducted either in a system in which an absorbefacient was used or in a system in which no absorbefacient was used, and the results were compared with those of Example 12 and studied. In Comparative Example 19, a comparative experiment was conducted in a system with or without an aliphatic acid, and the results were compared with those of Example 12. Moreover, in Reference Example 2, MOHRUS TAPE that was a tape preparation having no permeability was used, and the results were compared and investigated.

Example 12

To 15.3 g (83% by weight) of an acrylic adhesive agent (a 21.6% dope dissolved in ethyl acetate) obtained by copolymerizing the three components composed of 7% by weight of methyl methacrylate, 90% by weight of 2-ethylhexyl acrylate and 3% by weight of acrylic acid was added 45 ml of an ethyl acetate-ethanol solution mixture (ethyl acetate/ethanol volume ratio of 2/1). To the mixture were further added 0.1 g (2.5% by weight) of sorbitan monolaurate, 0.3 g (7.5% by weight) of glycerin, 0.24 g (6% by weight) of ketoprofen and 0.04 g (1% by weight) of magnesium stearate (StMg). The contents were stirred with a homogenizer to give a coating liquid for an adhesive drug layer of an adhesive tape preparation. A PET film treated with silicone was coated with the coating liquid by a doctor knife to form a coating layer (50 μm thick after drying), which was dried at 60° C. for 30 minutes to form an adhesive drug layer 50 μm thick. The adhesive drug layer was affixed to an air permeable woven fabric composed of a polyethylene terephthalate fiber, and subjected to the cutaneous absorption test, cohesive force test and permeability test. Table 4 shows the test results.

Example 13

An adhesive tape preparation was produced in the same manner as in Example 12 except that sorbitan monooleate was used for the adhesive drug layer in place of sorbitan monolaurate.

Table 4 shows the test results.

Example 14

An adhesive tape preparation was produced in the same manner as in Example 12 except that sorbitan trioleate was used for the adhesive drug layer in place of sorbitan monolaurate.

Table 4 shows the test results.

Example 15

An adhesive tape preparation was produced in the same manner as in Example 12 except that poly(oxyethylene) sorbitan monolaurate was used for the adhesive drug layer in place of sorbitan monolaurate.

Table 4 shows the test results.

Example 16

An adhesive tape preparation was produced in the same manner as in Example 12 except that poly(oxyethylene) sorbitan monopalmitate was used for the adhesive drug layer in place of sorbitan monolaurate.

Table 4 shows the test results.

Example 17

An adhesive tape preparation was produced in the same manner as in Example 12 except that poly(oxyethylene) sorbitan monostearate was used for the adhesive drug layer in place of sorbitan monolaurate.

Table 4 shows the test results.

Comparative Example 13

An adhesive tape preparation was produced in the same manner as in Example 12 except that the coating liquid for the adhesive drug layer contained 17.2 g of an acrylic adhesive agent, 0.24 g of ketoprofen and 0.04 g of magnesium stearate, and that the dried adhesive drug layer was composed of 93% by weight of the acrylic adhesive agent, 6% by weight of ketoprofen and 1% by weight of magnesium stearate.

Table 4 shows the test results.

Comparative Example 14

An adhesive tape preparation was produced in the same manner as in Example 12 except that the coating liquid for the adhesive drug layer contained 15.8 g of an acrylic adhesive agent, 0.3 g of glycerin, 0.24 g of ketoprofen and 0.04 g of magnesium stearate, and that the dried adhesive drug layer was composed of 85.5% by weight of the acrylic adhesive agent, 7.5% by weight of glycerin, 6% by weight of ketoprofen and 1% by weight of magnesium stearate.

Table 4 shows the test results.

Comparative Example 15

An adhesive tape preparation was produced in the same manner as in Example 12 except that the coating liquid for the adhesive drug layer contained 13.5 g of an acrylic adhesive agent, 0.8 g of isopropyl myristate, 0.24 g of ketoprofen and 0.04 g of magnesium stearate, and that the dried adhesive drug layer was composed of 73% by weight of the acrylic adhesive agent, 20% by weight of isopropyl myristate, 6% by weight of ketoprofen and 1% by weight of magnesium stearate.

Table 4 shows the test results.

Comparative Example 16

An adhesive tape preparation was produced in the same manner as in Example 12 except that the coating liquid for the adhesive drug layer contained 12.1 g of an acrylic adhesive agent, 0.3 g of glycerin, 0.8 g of isopropyl myristate, 0.24 g of ketoprofen and 0.04 g of magnesium stearate, and that the dried adhesive drug layer was composed of 65.5% by weight of the acrylic adhesive agent, 7.5% by weight of glycerin, 20% by weight of isopropyl myristate, 6% by weight of ketoprofen and 1% by weight of magnesium stearate.

Table 4 shows the test results.

Comparative Example 17

An adhesive tape preparation was produced in the same manner as in Example 12 except that the coating liquid for the adhesive drug layer contained 15.8 g of an acrylic adhesive agent, 0.4 g of sorbitan monolaurate, 0.24 g of ketoprofen and 0.04 g of magnesium stearate, and that the dried adhesive drug layer was composed of 83% by weight of the acrylic adhesive agent, 10% by weight of sorbitan monolaurate, 6% by weight of ketoprofen and 1% by weight of magnesium stearate.

Table 4 shows the test results.

Comparative Example 18

An adhesive tape preparation was produced in the same manner as in Example 12 except that the coating liquid for the adhesive drug layer contained 15.8 g of an acrylic adhesive agent, 0.4 g of poly(oxyethylene)sorbitan monolaurate, 0.24 g of ketoprofen and 0.04 g of magnesium stearate, and that the dried adhesive drug layer was composed of 83% by weight of the acrylic adhesive agent, 10% by weight of poly(oxyethylene)sorbitan monolaurate, 6% by weight of ketoprofen and 1% by weight of magnesium stearate.

Table 4 shows the test results.

Comparative Example 19

An adhesive tape preparation was produced in the same manner as in Example 12 except that the coating liquid for the adhesive drug layer contained 15.6 g of an acrylic adhesive agent, 0.1 g of sorbitan monolaurate, 0.3 g of glycerin and 0.24 g of ketoprofen, and that the dried adhesive drug layer was composed of 84% by weight of the acrylic adhesive agent, 2.5% by weight of sorbitan monolaurate, 7.5% by weight of glycerin and 6% by weight of ketoprofen.

Table 4 shows the test results.

Reference Example 2

MOHRUS TAPE was subjected to the same tests as in Example 12. Table 4 shows the test results.

In Examples 18 to 19 to be explained below, the relationship between an addition amount of sorbitan monolaurate and a permeated amount of ketoprofen, and the cohesive force and permeability of the adhesive drug layers containing the absorption promoters were investigated.

Example 18

An adhesive tape preparation was produced in the same manner as in Example 12 except that the coating liquid for the adhesive drug layer contained 14.9 g of an acrylic adhesive agent, 0.2 g of sorbitan monolaurate, 0.3 g of glycerin, 0.24 g of ketoprofen and 0.04 g of magnesium stearate, and that the dried adhesive drug layer was composed of 80.5% by weight of the acrylic adhesive agent, 5% by weight of sorbitan monolaurate, 7.5% by weight of glycerin, 6% by weight of ketoprofen and 1% by weight of magnesium stearate.

Table 4 shows the test results.

Example 19

An adhesive tape preparation was produced in the same manner as in Example 12 except that the coating liquid for the adhesive drug layer contained 13.9 g of an acrylic adhesive agent, 0.4 g of sorbitan monolaurate, 0.3 g of glycerin, 0.24 g of ketoprofen and 0.04 g of magnesium stearate, and that the dried adhesive drug layer was composed of 75.5% by weight of the acrylic adhesive agent, 10% by weight of sorbitan monolaurate, 7.5% by weight of glycerin, 6% by weight of ketoprofen and 1% by weight of magnesium stearate.

Table 4 shows the test results.

In Example 20 to be explained below, the relationship (compared with Example 12) between an addition amount of glycerin and a permeated amount of ketoprofen, and the cohesive force and permeability of an adhesive drug layer containing the absorption promoter were investigated.

Example 20

An adhesive tape preparation was produced in the same manner as in Example 12 except that the coating liquid for the adhesive drug layer contained 13.9 g of an acrylic adhesive agent, 0.1 g of sorbitan monolaurate, 0.6 g of glycerin, 0.24 g of ketoprofen and 0.04 g of magnesium stearate, and that the dried adhesive drug layer was composed of 75.5% by weight of the acrylic adhesive agent, 2.5% by weight of sorbitan monolaurate, 15% by weight of glycerin, 6% by weight of ketoprofen and 1% by weight of magnesium stearate.

Table 4 shows the test results.

In Examples 21 to 22 to be explained below, the relationship between an addition amount of isopropyl myristate and a permeated amount of ketoprofen, and the cohesive force and permeability of an adhesive drug layer containing the absorption promoter were investigated.

Example 21

An adhesive tape preparation was produced in the same manner as in Example 12 except that the coating liquid for the adhesive drug layer contained 13.5 g of an acrylic adhesive agent, 0.1 g of sorbitan monolaurate, 0.3 g of glycerin, 0.4 g of isopropyl myristate, 0.24 g of ketoprofen and 0.04 g of magnesium stearate, and that the dried adhesive drug layer was composed of 73% by weight of the acrylic adhesive agent, 2.5% by weight of sorbitan monolaurate, 7.5% by weight of glycerin, 10% by weight of isopropyl myristate, 6% by weight of ketoprofen and 1% by weight of magnesium stearate.

Table 4 shows the test results.

Example 22

An adhesive tape preparation was produced in the same manner as in Example 12 except that the coating liquid for the adhesive drug layer contained 11.7 g of an acrylic adhesive agent, 0.1 g of sorbitan laurate, 0.3 g of glycerin, 0.8 g of isopropyl myristate, 0.24 g of ketoprofen and 0.04 g of magnesium stearate, and that the dried adhesive drug layer was composed of 63.5% by weight of the acrylic adhesive agent, 2.5% by weight of sorbitan monolaurate, 7.5% by weight of glycerin, 20% by weight of isopropyl myristate, 6% by weight of ketoprofen and 1% by weight of magnesium stearate.

Table 4 shows the test results.

Comparative Example 20

An adhesive tape preparation was produced in the same manner as in Example 12 except that the coating liquid for the adhesive drug layer contained 13.5 g of an acrylic adhesive agent, 0.1 g of sorbitan monolaurate, 0.4 g of isopropyl myristate, 0.24 g of ketoprofen and 0.04 g of magnesium stearate, and that the dried adhesive drug layer was composed of 80.3% by weight of the acrylic adhesive agent, 2.5% by weight of sorbitan monolaurate, 10% by weight of isopropyl myristate, 6% by weight of ketoprofen and 1% by weight of magnesium stearate.

Table 4 shows the test results.

In Examples 23 to 24 to be explained below, the permeability of ketoprofen, and the cohesive force and permeability of an adhesive drug layer containing the absorption promoter were investigated when 1,2,6-hexanetriol was used in place of glycerin and isooctyl palmitate was used in place of isooctyl myristate.

Example 23

An adhesive tape preparation was produced in the same manner as in Example 12 except that the coating liquid for the adhesive drug layer contained 15.3 g of an acrylic adhesive agent, 0.1 g of sorbitan monolaurate, 0.3 g of 1,2,6-hexanetriol, 0.24 g of ketoprofen and 0.04 g of magnesium stearate, and that the dried adhesive drug layer was composed of 83% by weight of the acrylic adhesive agent, 2.5% by weight of sorbitan monolaurate, 7.5% by weight of 1,2,6-hexanetriol, 6% by weight of ketoprofen and 1% by weight of magnesium stearate.

Table 4 shows the test results.

Example 24

An adhesive tape preparation was produced in the same manner as in Example 12 except that the coating liquid for the adhesive drug layer contained 13.5 g of an acrylic adhesive agent, 0.1 g of sorbitan monolaurate, 0.3 g of glycerin, 0.4 g of isooctyl palmitate, 0.24 g of ketoprofen and 0.04 g of magnesium stearate, and that the dried adhesive drug layer was composed of 73% by weight of the acrylic adhesive agent, 2.5% by weight of sorbitan monolaurate, 7.5% by weight of glycerin, 10% by weight of isooctyl palmitate, 6% by weight of ketoprofen and 1% by weight of magnesium stearate.

Table 4 shows the test results.

TABLE 4

|  | Additives | | Permeated amount of ketoprofen ($\mu g/cm^2 \cdot 24$ hr) | Cohesive force (prevention of adhesion retention of adhesive drug layer) | Permeability ($g/m^2 \cdot day$) |
|---|---|---|---|---|---|
| Ex. 12 | Span20 | 2.5 wt. % | 80 | ○ | 743 |
|  | GC | 7.5 wt. % | | | |
|  | StMg | 1.0 wt. % | | | |
| Ex. 13 | Span80 | 2.5 wt. % | 60 | ○ | 762 |
|  | GC | 7.5 wt. % | | | |
|  | StMg | 1.0 wt. % | | | |

TABLE 4-continued

|  | Additives |  | Permeated amount of ketoprofen ($\mu g/cm^2 \cdot 24\ hr$) | Cohesive force (prevention of adhesion retention of adhesive drug layer) | Permeability ($g/m^2 \cdot day$) |
|---|---|---|---|---|---|
| Ex. 14 | Span85 | 2.5 wt. % | 40 | ○ | 757 |
|  | GC | 7.5 wt. % |  |  |  |
|  | StMg | 1.0 wt. % |  |  |  |
| Ex. 15 | TWEEN20 | 2.5 wt. % | 53 | ○ | 498 |
|  | GC | 7.5 wt. % |  |  |  |
|  | StMg | 1.0 wt. % |  |  |  |
| Ex. 16 | TWEEN40 | 2.5 wt. % | 48 | ○ | 521 |
|  | GC | 7.5 wt. % |  |  |  |
|  | StMg | 1.0 wt. % |  |  |  |
| Ex. 17 | TWEEN60 | 2.5 wt. % | 42 | ○ | 512 |
|  | GC | 7.5 wt. % |  |  |  |
|  | StMg | 1.0 wt. % |  |  |  |
| Comp. Ex. 13 | StMg | 1.0 wt. % | 24 | ○ | 504 |
| Comp. Ex. 14 | GC | 7.5 wt. % | 7 | ○ | 689 |
|  | StMg | 1.0 wt. % |  |  |  |
| Comp. Ex. 15 | IPM | 20 wt. % | 17 | ○ | 512 |
|  | StMg | 1.0 wt. % |  |  |  |
| Comp. Ex. 16 | GC | 7.5 wt. % | 20 | ○ | 677 |
|  | IPM | 7.5 wt. % |  |  |  |
|  | StMg | 1.0 wt. % |  |  |  |
| Comp. Ex. 17 | Span20 | 10 wt. % | 60 | X | 457 |
|  | StMg | 1.0 wt. % |  |  |  |
| Comp. Ex. 18 | TWEEN20 | 10 wt. % | 35 | X | 500 |
|  | StMg | 1.0 wt. % |  |  |  |
| Comp. Ex. 19 | Span20 | 2.5 wt. % | 82 | X | 722 |
|  | GC | 7.5 wt. % |  |  |  |
| Ref. Ex. 2 | MOHRUS TAPE |  | 40 | ○ | 0 |
| Ex. 18 | Span20 | 5 wt. % | 132 | ○ | 738 |
|  | GC | 7.5 wt. % |  |  |  |
|  | StMg | 1.0 wt. % |  |  |  |
| Ex. 19 | Span20 | 10 wt. % | 160 | ○ | 744 |
|  | GC | 7.5 wt. % |  |  |  |
|  | StMg | 1.0 wt. % |  |  |  |
| Ex. 20 | Span20 | 2.5 wt. % | 100 | ○ | 787 |
|  | GC | 15 wt. % |  |  |  |
|  | StMg | 1.0 wt. % |  |  |  |
| Ex. 21 | Span20 | 2.5 wt. % | 105 | ○ | 721 |
|  | GC | 7.5 wt. % |  |  |  |
|  | IPM | 10 wt. % |  |  |  |
|  | StMg | 1.0 wt. % |  |  |  |
| Ex. 22 | Span20 | 2.5 wt. % | 121 | ○ | 761 |
|  | GC | 7.5 wt. % |  |  |  |
|  | IPM | 20 wt. % |  |  |  |
|  | StMg | 1.0 wt. % |  |  |  |
| Comp. Ex. 20 | Span20 | 2.5 wt. % | 78 | X | 743 |
|  | IPM | 10 wt. % |  |  |  |
|  | StMg | 1.0 wt. % |  |  |  |
| Ex. 23 | Span20 | 2.5 wt. % | 70 | ○ | 744 |
|  | 1,2,6-hexanetriol | 7.5 wt. % |  |  |  |
|  | StMg | 1.0 wt. % |  |  |  |
| Ex. 24 | Span20 | 2.5 wt. % | 97 | ○ | 723 |
|  | GC | 7.5 wt. % |  |  |  |
|  | IOP | 10 wt. % |  |  |  |
|  | StMg | 1.0 wt. % |  |  |  |

Note:
SPAN20 = sorbitan monolaurate
SPAN80 = sorbitan monooleate
SPAN85 = sorbitan trioleate
GC = glycerin
StMg = magnesium stearate
TWEEN20 = poly(oxyethylene) sorbitan monolaurate
TWEEN40 = poly(oxyethylene) sorbitan monopalmitate
TWEEW60 = poly(oxyethylene) sorbitan monostearate
IPM = isopropyl myristate
IOP = isooctyl palmitate In Example 25, felbinac was used as a nonsteroidal antiphlogistic antalgic in place of ketoprofen, and the permeability, and the cohesive force and permeability of an adhesive drug layer containing the medicine were investigated.

Example 25

An adhesive tape preparation was produced in the same manner as in Example 12 except that the coating liquid for the adhesive drug layer contained 16.4 g of an acrylic adhesive agent, 0.1 g of sorbitan monolaurate, 0.3 g of glycerin, 0.04 g of felbinac and 0.04 g of magnesium stearate, and that the dried adhesive drug layer was composed of 88.5% by weight of the acrylic adhesive agent, 2.5% by weight of sorbitan monolaurate, 7.5% by weight of glycerin, 0.5% by weight of felbinac and 1% by weight of magnesium stearate.

Table 5 shows the test results.

Reference Example 3

Cell Touch (trade name, poultice) was subjected to the same permeability test for felbinac and the same cohesive force test as in Example 25.

Table 5 shows the test results.

TABLE 5

|  | Additives | | Permeated amount of felbinac ($\mu$g/cm$^2$ · 24 hr) | Cohesive force | Permeability (g/m$^2$ · day) |
| --- | --- | --- | --- | --- | --- |
| Ex. 25 | Span20 | 2.5 wt. % | 4.2 | good | 722 |
|  | GC | 7.5 wt. % |  |  |  |
|  | StMg | 1.0 wt. % |  |  |  |
| Ref. Ex. 3 | Cell Touch (trade name) | | 4.0 | good | — |

Note:
SPAN20 = sorbitan monolaurate
GC = glycerin
StMg = magnesium stearate

Estradiol was used as a female sex hormone agent in Examples 26 to 27, to be explained below, and the permeability of estradiol of the adhesive drug layer, and the cohesive force and permeability of the adhesive drug layer containing the drug were investigated. Moreover, in order to achieve the high permeability of estradiol, the same investigation was performed in Example 28, to be explained below, in a system in which ethyl oleate and polyvinylpyrrolidone were added.

Example 26

An adhesive tape preparation was produced in the same manner as in Example 12 except that the coating liquid for the adhesive drug layer contained 14.0 g of an acrylic adhesive agent, 0.1 g of sorbitan monolaurate, 0.3 g of glycerin, 0.128 g of estradiol and 0.04 g of magnesium stearate, and that the dried adhesive drug layer was composed of 75.8% by weight of the acrylic adhesive agent, 2.5% by weight of sorbitan monolaurate, 7.5% by weight of glycerin, 3.2% by weight of estradiol and 1% by weight of magnesium stearate. Table 6 shows the test results.

Example 27

An adhesive tape preparation was produced in the same manner as in Example 12 except that the coating liquid for the adhesive drug layer contained 14.0 g of an acrylic adhesive agent, 0.1 g of sorbitan monolaurate, 0.3 g of glycerin, 0.4 g of isopropyl myristate, 0.128 g of estradiol and 0.04 g of magnesium stearate, and that the dried adhesive drug layer was composed of 75.8% by weight of the acrylic adhesive agent, 2.5% by weight of sorbitan monolaurate, 7.5% by weight of glycerin, 10% by weight of isopropyl myristate, 3.2% by weight of estradiol and 1% by weight of magnesium stearate. Table 6 shows the test results.

Example 28

An adhesive tape preparation was produced in the same manner as in Example 12 except that the coating liquid for the adhesive drug layer contained 8.3 g of an acrylic adhesive agent, 0.2 g of sorbitan monolaurate, 0.4 g of isopropyl myristate, 0.6 g of 1,2,6-hexanetriol, 0.6 g of ethyl oleate, 0.24 g of polyvinylpyrrolidone, 0.16 g of estradiol and 0.04 g of magnesium stearate, and that the dried adhesive drug layer was composed of 45% by weight of the acrylic adhesive agent, 5% by weight of sorbitan monolaurate, 10% by weight of isopropyl myristate, 15% by weight of 1,2,6-hexanetriol, 15% by weight of ethyl oleate, 6% by weight of polyvinylpyrrolidone, 4% by weight of estradiol and 1% by weight of magnesium stearate. Table 6 shows the test results.

Comparative Example 21

An adhesive tape preparation was produced in the same manner as in Example 12 except that the coating liquid for the adhesive drug layer contained 17.7 g of an acrylic adhesive agent, 0.128 g of estradiol and 0.04 g of magnesium stearate, and that the dried adhesive drug layer was composed of 95.8% by weight of the acrylic adhesive agent, 3.2% by weight of estradiol and 1% by weight of magnesium stearate. Table 6 shows the test results.

TABLE 6

|  | Additives | | Permeated amount of estradiol ($\mu$g/cm$^2$ · 48 hr) | Cohesive force (prevention of adhesion retention of adhesive drug layer) | Permeability (g/m$^2$ · day) |
| --- | --- | --- | --- | --- | --- |
| Ex. 26 | Span20 | 2.5 wt. % | 20 | ○ | 724 |
|  | GC | 7.5 wt. % |  |  |  |
|  | StMg | 1.0 wt. % |  |  |  |

TABLE 6-continued

| | Additives | | Permeated amount of estradiol ($\mu$g/cm$^2$ · 48 hr) | Cohesive force (prevention of adhesion retention of adhesive drug layer) | Permeability (g/m$^2$ · day) |
|---|---|---|---|---|---|
| Ex. 27 | Span20 | 2.5 wt. % | 15.7 | ◯ | 716 |
| | GC | 2.5 wt. % | | | |
| | IPM | 10 wt. % | | | |
| | StMg | 1.0 wt. % | | | |
| Ex. 28 | Span20 | 5 wt. % | 35 | ◯ | 720 |
| | IPM | 10 wt. % | | | |
| | 1,2,6-hexanetriol | 15 wt. % | | | |
| | OE | 15 wt. % | | | |
| | PVP | 6 | | | |
| | StMg | — wt. % | | | |
| Comp. Ex. 21 | StMg | 1.0 wt. % | 1.1 | ◯ | 515 |

Note:
SPAN20 = sorbitan monolaurate
GC = glycerin
StMg = magnesium stearate
IPM = isopropyl myristate
OE = ethyl oleate
PVP = polyvinylpyrrolidone Testosterone was used as a male sex hormone in Examples 29 to 30, to be explained below, and the permeability of the drug, and the cohesive force and permeability of the adhesive drug layer containing the drug were investigated.

Example 29

An adhesive tape preparation was produced in the same manner as in Example 12 except that the coating liquid for the adhesive drug layer contained 15.9 g of an acrylic adhesive agent, 0.1 g of sorbitan monolaurate, 0.3 g of glycerin, 0.128 g of testosterone and 0.04 g of magnesium stearate, and that the dried adhesive drug layer was composed of 85.8% by weight of the acrylic adhesive agent, 2.5% by weight of sorbitan monolaurate, 7.5% by weight of glycerin, 3.2% by weight of testosterone and 1% by weight of magnesium stearate. Table 7 shows the test results.

Example 30

An adhesive tape preparation was produced in the same manner as in Example 12 except that the coating liquid for the adhesive drug layer contained 14.0 g of an acrylic adhesive agent, 0.1 g of sorbitan monolaurate, 0.3 g of glycerin, 0.4 g of isopropyl myristate, 0.128 g of testosterone and 0.04 g of magnesium stearate, and that the dried adhesive drug layer was composed of 75.8% by weight of the acrylic adhesive agent, 2.5% by weight of sorbitan monolaurate, 7.5% by weight of glycerin, 10% by weight of isopropyl myristate, 3.2% by weight of testosterone and 1% by weight of magnesium stearate. Table 7 shows the test results.

Comparative Example 22

An adhesive tape preparation was produced in the same manner as in Example 12 except that the coating liquid for the adhesive drug layer contained 17.7 g of an acrylic adhesive agent, 0.128 g of testosterone and 0.04 g of magnesium stearate, and that the dried adhesive drug layer was composed of 95.8% by weight of the acrylic adhesive agent, 3.2% by weight of testosterone and 1% by weight of magnesium stearate. Table 7 shows the test results.

TABLE 7

| | Additives | | Permeated amount of testosterone ($\mu$g/cm$^2$ · 48 hr) | Cohesive force (prevention of adhesion retention of adhesive drug layer) | Permeability (g/m$^2$ · day) |
|---|---|---|---|---|---|
| Ex. 29 | Span20 | 2.5 wt. % | 5.1 | ◯ | 752 |
| | GC | 7.5 wt. % | | | |
| | StMg | 1.0 wt. % | | | |
| Ex. 30 | Span20 | 2.5 wt. % | 6.2 | ◯ | 734 |
| | GC | 7.5 wt. % | | | |
| | IPM | 10 wt. % | | | |
| | StMg | 1.0 wt. % | | | |
| Comp. Ex. 22 | StMg | 1.0 wt. % | 2.5 | ◯ | 485 |

Tables 2 to 7 show that the adhesive drug layer of the adhesive tape preparation in the present invention has good cohesive force (prevention of adhesion retention), peeling strength, permeability and the like. Tables 3 to 7 show that the adhesive drug of the present invention has good permeability of the drug (cutaneous absorption).

Industrial Applicability

The adhesive agent composition and the adhesive tape of the present invention have good adhesion and permeability. Moreover, the adhesive drug composition and adhesive tape preparation of the present invention have good adhesion and permeability, and further shows good permeability of the drug (cutaneous absorption). The effective drug can be subjected to cutaneous absorption without stimulation of the skin. Accordingly, the adhesive agent composition, adhesive tape, adhesive drug composition and adhesive tape preparation of the present invention can be industrially effectively utilized.

What is claimed is:

1. A permeable adhesive tape comprising a substrate and an adhesive layer formed on one side of the substrate and containing the adhesive agent composition comprising 50 to 90% by weight of an acrylic adhesive agent, 2.5 to 50% by weight of a polyhydric alcohol-containing liquid component, and 0.1 to 10% by weight of an aliphatic acid metal salt formed from an aliphatic acid that has a hydrocarbon group containing 8 to 18 carbon atoms and a mono- to tri-valence metal, the polyhydric alcohol-containing liquid component containing, in addition to the polyhydric alcohol, at least one sorbitan ester compound selected from sorbitan esters and poly (oxyalkylene) sorbitan esters of aliphatic acids having a hydrocarbon group having 12 to 18 carbon atoms, in an amount of 0.5 to 20% by weight based on the total weight of the composition, wherein the substrate comprises an air and water vapor-permeable nonwoven, woven, or knitted fabric or porous film, and the adhesive layer has a thickness of 5 to 1,000 μm; and the adhesive tape has as a whole, a water vapor permeability of at least 300 g/m²·day.

2. The permeable adhesive tape according to claim 1, wherein the acrylic adhesive agent contains at least one polymer selected from the group consisting of homopolymers of acrylic acid, methacrylic acid, an alkyl acrylate and an alkyl methacrylate, and copolymers containing at least one of the above monomer components.

3. The permeable adhesive tape according to claim 1, wherein the polyhydric alcohol-containing liquid component contains from 1 to 30% by weight of a polyhydric alcohol based on the weight of the entire composition.

4. The permeable adhesive tape according to claim 1, wherein the polyhydric alcohol in the polyhydric alcohol-containing liquid component is selected from glycerin, propylene glycol, 1,3-butylene glycol, diglycerin, dipropylene glycol, 1,2,6-hexanetriol, sorbitol polyethylene glycol and pentaerythritol.

5. The permeable adhesive tape according to claim 1, wherein the polyhydric alcohol-containing liquid component contains, in addition to the polyhydric alcohol and sorbitan ester compound, at least one substance selected from aliphatic esters different from the sorbitan ester compound and polyvinylpyrrolidone.

6. The permeable adhesive tape according to claim 5, wherein the content of the aliphatic ester in the polyhydric alcohol-containing liquid component is from 1 to 30% by weight based on the weight of the entire composition.

7. The permeable adhesive tape according to claim 5, wherein the aliphatic ester is selected from isopropyl myristate, isopropyl palmitate, isooctyl palmitate, ethyl oleate and diethyl sebacate.

8. The permeable adhesive tape according to claim 1, wherein the aliphatic acid having a hydrocarbon group containing 8 to 18 carbon atoms in the aliphatic acid metal salt is selected from lauric acid, myristic acid, stearic acid and oleic acid, and the mono- to trivalent metal is selected from sodium, magnesium, zinc and aluminum.

9. The permeable adhesive tape according to claim 1, further comprising a drug mixed with the adhesive agent composition in the adhesive layer.

10. The permeable adhesive tape according to claim 9, wherein the drug is present in an amount of 0.05 to 40% weight based on the weight of the adhesive agent composition.

11. The permeable adhesive tape according to claim 9, wherein the drug is selected from nonsteroidal anti-flammatory agents, antihypertensives, local anesthetics, antibiotics, calcium antagonists, cardiotonics, antiepileptics, hypotensive diuretics, antifungals, antiallergics, antihistaminics, anti-cancer agents, antipsychotropics, anti-vertigo agents, sleep controller agents, coronary vasodilators, hormones, hypotensors, treating agents for asthma, treating agents for nositis, hypoglycemics and anti-ulcer agents.

12. The premeable adhesive tape according to claim 9, wherein the substrate permits no transmission or diffusion of the drug.

13. The premeable adhesive tape according to any one of claims 1 and 2 to 12, wherein the substrate comprises at least one member selected from polyethylene-based, polypropylene-based, polyester-based, polyamide-based, polytetrafluoroethylene-based, polyvinyl chloride-based and polyurethane-based polymers.

* * * * *